United States Patent [19]

Roling

[11] Patent Number: 4,929,778
[45] Date of Patent: May 29, 1990

[54] METHODS AND COMPOSITIONS FOR INHIBITING STYRENE POLYMERIZATION

[75] Inventor: Paul V. Roling, Spring, Tex.

[73] Assignee: Betz Laboratories, Inc., Trevose, Pa.

[21] Appl. No.: 361,170

[22] Filed: Jun. 5, 1989

[51] Int. Cl.$^5$ .............................................. C07C 7/20
[52] U.S. Cl. .......................................... 585/3; 585/2; 585/4; 585/5; 252/403
[58] Field of Search ............................... 585/5, 2, 3, 4; 252/403

[56] References Cited

U.S. PATENT DOCUMENTS 4,466,905  8/1984  Butler et al. ............................ 585/5

FOREIGN PATENT DOCUMENTS 0240297  10/1987  European Pat. Off. ............... 585/2
0120521  9/1980   Japan ..................................... 585/3
0763313  9/1980   U.S.S.R. ................................ 585/5
1098200  5/1986   U.S.S.R. ................................ 585/5

OTHER PUBLICATIONS

"An Investigation of the Synergism between N-Isopropyl-N'-phenyl-1,4-phenylenediamine and 2,6-Dialkylphenols", L. Taimr and J. Pospisil, Die Angewandte Makromolekulare Chemie 128 (1984) 181-188 (Nr. 2038).

"A Cooperative Effect between Antioxidants N-Iso-Propyl-N'-Phenyl-1,4-Phenylene Diamine and 2,6-Di-tertbutylphenol", L. Taimr & J. Pospisil, Polymer Degradation and Stability 8, (1984) 23-35.

Primary Examiner—Curtis R. Davis
Attorney, Agent, or Firm—Alexander D. Ricci; Bruce E. Peacock

[57] ABSTRACT

Methods and compositions are provided for inhibiting the polymerization of styrene monomer during elevated temperature processing thereof or during storage or shipment of styrene containing product. The compositions comprise a combination of (a) a phenylenediamine compound having at least one N-H bond and (b) a hindered phenol compound. The methods comprise adding from 1-10,000 ppm of the combination to the styrene medium, per one million parts of styrene.

30 Claims, No Drawings

METHODS AND COMPOSITIONS FOR INHIBITING STYRENE POLYMERIZATION

FIELD OF THE INVENTION

The present invention pertains to methods and compositions for inhibiting the undesired polymerization of vinyl aromatic monomers, such as styrene monomer, during processes such as monomer preparation, and purification, and during storage and shipment of products containing such monomers.

BACKGROUND OF THE INVENTION

Polystyrene is a thermoplastic with many desirable characteristics. It is clear, transparent, readily colored and easily fabricated. The family of styrene polymers includes polystyrene itself, copolymers of styrene with other vinyl monomers, polymers of derivatives of styrene and mixtures of polystyrene and styrene-containing copolymers with elastomers.

ABS (acrylonitrile, butadiene-styrene) resins have enjoyed tremendous commercial popularity for many years as durable, temperature and solvent resistant elastomers. On the other hand, styrene plastics are commonly used for packaging, including foams and films, coatings, in appliance fabrication, for housewares and toys, lighting fixtures and in construction materials.

It is well known that styrene monomer readily polymerizes when heated or exposed to light. Heat polymerization is rapid. In fact, polymerization increases with increasing temperature. This polymerization is undesirable during many stages of the manufacturing, processing, handling, storage and use of styrene monomers.

Common industrial methods for producing styrene include a variety of purification processes, including distillation, to remove impurities. Unfortunately, purification operations carried out at elevated temperatures result in an increased rate of undesired polymerization. Polymerization, such as thermal polymerization, during the monomer purification process, results not only in loss of desired monomer end-product, but also in loss of production efficiency caused by polymer formation or agglomeration on process equipment. In heat requiring operations, such agglomeration adversely affects heat transfer efficiency.

PRIOR ART

Phenylenediamines and phenols, singly, are well known in the art as styrene polymerization inhibitors. Tamir et al, in *Angew. McKromol. Chem.*, 128, 181–188(1984) and *Polymer Degrad. Stabil.*, 8, 23–35(1985) suggest that phenylenediamines and 2,6-disubstituted hindered phenols exhibit synergism as antioxidants and stabilizers for rubber compositions. However, there is no hint or suggestion in these articles that the combination could be successfully employed as a styrene polymerization inhibitor, nor is there any suggestion therein as to the use of a hindered phenol compound having a substituent located in the para position relative to the hydroxyl group of the phenol. This latter characteristic, as shown hereinafter, is important in providing enhanced styrene polymerization inhibition performance.

DETAILED DESCRIPTION OF THE PREFERRED EMBODIMENT

In accordance with the invention, both a phenylenediamine compound and a hindered phenol are conjointly utilized to inhibit polymerization of a vinyl aromatic monomer such as styrene.

By hindered phenol, I mean a phenolic compound having substituents located at both of the ortho positions relative to the hydroxyl group as well as at the para position relative to the hydroxyl group. A wide variety of such substituents may be chosen. For example, the ortho and para position substituents may comprise $C_1$–$C_{20}$ alkyl, $C_1$–$C_{30}$ alkaryl, substituted $C_1$–$C_{30}$ alkaryl, thiophenol, substituted thiophenol, $C_1$–$C_{40}$ alkanoic acid ester, $C_1$–$C_6$ alkyamino, polynuclear aryl, substituted polynuclear aryl, $C_1$–$C_6$ alkoxy, and amine groupings.

The hindered phenols in accordance with the invention may be represented by the formula

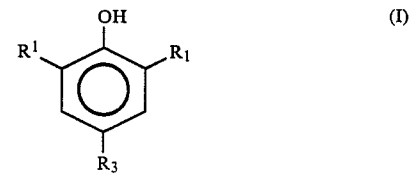

wherein $R_1$ and $R_2$ may be the same or different, with $R_1$ and $R_2$ being independently chosen and selected from the group of $C_1$–$C_{20}$ alkyl, $C_1$–$C_{30}$ alkaryl, and substituted $C_1$–$C_{30}$ alkaryl. $R_3$ may be selected from $C_1$–$C_{20}$ alkyl, thiophenol, substituted thiophenol, $C_1$–$C_{40}$ alkanoic acid ester, $C_1$–$C_{30}$ alkaryl, substituted $C_1$–$C_{30}$ alkaryl, $C_1$–$C_6$ alkylamino, $C_1$–$C_6$ alkoxy, amine, polynuclear aryl and substituted polynuclear aryl.

At present, preferred hindered phenols include:
2,6-di-t-butyl-4-methylphenol
4,4'-thiobis-(6-t-butyl-2-methylphenol)
and octadecyl 3-(3',5'-di-t-butyl-4'-hydroxyphenyl)-propionate.

These three hindered phenols are all commercially available.

Other hindered phenol compounds that may be listed as being exemplary include
4,4'-methylenebis(2,6-di-t-butylphenol)
1,3,5-trimethyl-2,4,6-tris(3,5-di-t-butyl-4-hydroxybenzyl)benzene
2,6-di-t-butyl-α-dimethylamino-p-cresol
2,6-di-t-butyl-4-secbutylphenol
2,2'-methylenebis(4-ethyl-6-t-butylphenol)
2,2'-methylenebis(4-methyl-6-t-butylphenol)
2,2'-methylenebis(6-(1-methylcyclohexyl)-p-cresol; and
2,2'-methylenebis(4-methyl-6-cyclohexylphenol)

In accordance with structural formula I supra the preferred hindered phenols are those wherein $R_1$ and $R_2$ are chosen from $C_1$–$C_{20}$ tert-alkyl and $C_1$–$C_{20}$ alkyl with $R_3$ being chosen from $C_1$–$C_{20}$ alkyl, $C_1$–$C_{40}$ alkanoic acid ester, thiophenol and substituted thiophenol having the structure

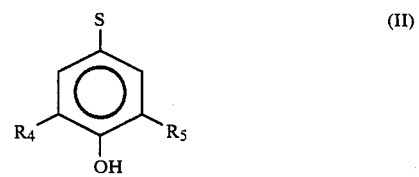

with $R_4$ and $R_5$ being independently selected from $C_1-C_6$ alkyl. Preferably one of $R_4$ and $R_5$ is a tert-alkyl grouping.

As to the phenylenediamines that may be used, these include the phenylenediamines having at least one N—H bond. It is thought that o-phenylenediamine or derivatives thereof having at least one N—H bond are suitable in accordance with the instant invention.

However, the preferred phenylenediamines are the p-phenylenediamines having the structure

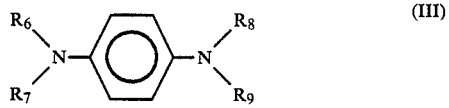

(III)

wherein $R_6$, $R_7$, $R_8$, and $R_9$ are the same of different and are hydrogen, alkyl, aryl, alkaryl, or aralkyl groups with the proviso that at least one of $R_6$, $R_7$, $R_8$, or $R_9$ is hydrogen. More preferably, the alkyl, aryl, alkaryl, and aralkyl groups have one to about twenty carbon atoms. The alkyl, aryl, alkaryl, and aralkyl groups may be straight or branched-chain groups. Exemplary p-phenylenediamines include p-phenylenediamine wherein $R_6$, $R_7$, $R_8$, and $R_9$ are hydrogen; N-phenyl-N'-alkyl-p-phenylenediamines such as, N-phenyl-N'-methyl-p-phenylenediamine, N-phenyl-N'-ethyl-p-phenylenediamine, N-phenyl-N'-n-propyl-p-phenylenediamine, N-phenyl-N'-isopropyl-p-phenylenediamine, N-phenyl-N'-n-butyl-p-phenylenediamine, N-phenyl-N'-isobutyl-p-phenylenediamine, N-phenyl-N'-sec-butyl-p-phenylenediamine, N-phenyl-N'-tert-butyl-p-phenylenediamine, N-phenyl-N'-n-pentyl-p-phenylenediamine, N-phenyl-N'-n-hexyl-p-phenylenediamine, N-phenyl-N'-(1-methylhexyl)-p-phenylenediamine, N-phenyl-N'-(1,3-dimethylbutyl)-p-phenylenediamine, N-phenyl-N'-(1,4-dimethylpentyl)-p-phenylenediamine; N-phenyl-N',N'-dialkyl-p-phenylenediamines such as N-phenyl-N',N'-dimethyl-p-phenylenediamine, N-phenyl-N',N'-diethyl-p-phenylenediamine, N-phenyl-N',N'-di-n-butyl-p-phenylenediamine, N-phenyl-N',N'-di-sec-butyl-p-phenylenediamine, N-phenyl-N'-methyl-N'-ethyl-p-phenylenediamine; N,N-dialkyl-p-phenylenediamines such as N,N-dimethyl-p-phenylenediamine, and N,N-diethyl-p-phenylenediamine; N,N'-dialkyl-p-phenylenediamines such as N,N'-dimethyl-p-phenylenediamine, N,N'-diethyl-p-phenylenediamine, and N,N'-di-isopropyl-p-phenylenediamine; N,N'-diaryl-p-phenylenediamines such as N,N'-diphenyl-p-phenylenediamine; N,N,N'-trialkyl-p-phenylenediamines such as N,N,N'-trimethyl-p-phenylenediamine, and N,N,N'-triethyl-p-phenylenediamine. Preferably, the p-phenylenediamine is selected from the group consisting of N-phenyl-N'-(1,3-dimethylbutyl)-p-phenylenediamine and N-phenyl-N'-(1,4-dimethylpentyl)-p-phenylenediamine.

The total amount of phenylenediamine or derivatives thereof having at least one N—H group and hindered phenol used in the methods of the present invention as a polymerization inhibitor is that amount which is sufficient to effect inhibition of polymerization and will, of course, vary according to the conditions under which the styrene monomer is synthesized, processed, and/or stored. At higher temperatures, larger amounts of the anti-polymerization treatment are generally required. Preferably, the total amount of combined treatment (i.e., phenylenediamine or derivative thereof having at least one N—H group and hindered phenol) is from about 1 ppm to about 10,000 ppm combined treatment based on the weight of the monomer. Most preferably, the total amount of the aforesaid compounds is from 1 ppm to about 1,000 ppm based on the weight of the monomer. The weight ratios of phenylenediamine or derivatives thereof having at least one N—H group to hindered phenol, having a substituent located para to the hydroxyl, are preferably in the range of about 2:1 to about 1:2. Most preferably, the weight ratio of phenylenediamine or derivative thereof having at least one N—H group to hindered phenol is about 1:1.

The method of the present invention can control the fouling of processing equipment, such as the equipment used in separation and purification processes of styrene monomer, which is due to or caused by the polymerization of the monomer. The instant invention may be used as both a process inhibitor, which is employed during preparation and processing (e.g., employing heat) of the styrene monomer, and as a product inhibitor, which is combined with the styrene in order to inhibit polymerization during storage and handling. The phenylenediamine or derivative thereof having at least one N—H group and para substituted hindered phenol can be added to the styrene monomer by any conventional method. The components can be added to the monomer as a single composition containing the inhibitor compounds or the individual components can be added separately or in any other desired combination. The composition may be added as either a dispersion or as a solution using a suitable liquid carrier dispersing medium or solvent which is compatible with the styrene monomer. Preferably, a solution is provided and the solvent is a non-polar organic solvent such as xylene (a commercial mixture of o, m, and p isomers), or heavy aromatic naphtha.

Based upon presently available data, the composition preferred for use is N-phenyl-N'-(1,4-dimethylpentyl)-p-phenylenediamine and 2,6-di-t-butyl-4-methylphenol in a 1:1 weight ratio dissolved in heavy aromatic naphtha.

The data set forth below were developed and demonstrate the unexpected results occasioned by use of the invention. The following examples are included as being illustrations of the invention and should not be construed as limiting the scope thereof.

EXAMPLES

In order to demonstrate efficacy in inhibiting styrene polymerization, styrene was distilled twice under vacuum to remove the storage inhibitor. 10 ml of distilled styrene and candidate polymerization inhibitor (or blank for control) were added to a 17 ml test tube. The test tube was sealed with a tight fitting septum cap that was wired on. Two needles were placed in the septum and the tube was purged for 60 seconds with argon. The test tube was then placed in an oil bath at 225° F. for 3.0 hours. At the end of this time, the styrene was mixed with 90 ml of methanol, filtered, dried, and weighed. The percent polymerization inhibition protection was calculated by the equation $$\% \text{ protection} = \frac{[(\text{grams of polymer in the blank}) - (\text{grams of polymer in treated sample})] \times 100}{(\text{grams of polymer in the blank})}$$

Results are indicated in Tables I and II.

TABLE I

| Compound | ppm | % Protection | Average |
|---|---|---|---|
| RROA | 12.5 | 25 | 25 |
| | 25 | 6, 28, 29, 26, 17, 27, 23, 32, 27, 32, 30, 41, 49, 21, 41, 39, 47 | 30 |
| | 50 | 28, 33, 29, 21, 36, 23, 30, 84 | 36 |
| | 100 | 52, 53, 53, 43, 57, 65, 62 | 55 |
| A0-736 | 50 | 3, 6, 6 | 5 |
| | 100 | 8, 7 | 8 |
| BHT | 12.5 | 16 | 16 |
| | 25 | 3, 2, 1, 3, 16, 17, 4, 14 | 8 |
| | 50 | 1, 22 | 12 |
| | 100 | 9 | 9 |
| E-376 | 50 | 2 | 2 |
| | 100 | 3 | 3 |
| DTBP | 25 | 1, 1 | 1 |
| | 100 | 4 | 4 |

RROA is N-phenyl-N'-(1,4-dimethylpentyl)-p-phenylene-diamine, commercially available.
A0-736 is 4,4'-thiobis(6-t-butyl-2-methylphenol), commercially available.
BHT is 2,6-di-t-butyl-4-methylphenol, commercially available.
E-376 is octadecyl 3-(3',5'-di-t-butyl-4'-hydroxyphenyl)-propionate, commercially available.
DTBP is 2,6-di-t-butylphenol, commercially available.

TABLE II
Percent Protection of the Combinations of Components

| RROA ppm | Phenol ppm | Found % Protection | Calculated Additivity |
|---|---|---|---|
| A0-736 | | | |
| 25 | 75 | 32 | 36 |
| 50 | 50 | 56 | 41 |
| 50 | 75 | 66 | 42 |
| 50 | 100 | 58 | 44 |
| 100 | 50 | 76 | 60 |
| 100 | 100 | 97, 83 = 90 ave | 63 |
| BHT | | | |
| 12.5 | 12.5 | 45 | 41 |
| 25 | 25 | 33, 20, 70, 72, 39 = 47 ave | 38 |
| 25 | 75 | 21 | 40 |
| 50 | 50 | 48, 59 = 54 ave | 48 |
| 50 | 100 | 61 | 45 |
| 100 | 50 | 88 | 67 |
| 100 | 100 | 91, 98 = 95 ave | 64 |
| E-376 | | | |
| 25 | 75 | 19 | 32 |
| 50 | 50 | 41 | 38 |
| 50 | 100 | 51 | 39 |
| 100 | 50 | 58 | 57 |
| 100 | 100 | 78 | 58 |
| DTBP | | | |
| 25 | 25 | 29, 34 = 32 ave | 31 |
| 100 | 100 | 54 | 59 |

Calculated Additivity is the % protection calculated by the addition of the appropriate RROA and phenol averages from Table I.

DISCUSSION

Based upon Tables I and II, the combinations of phenylenediamine compound (RROA) and hindered phenol in accordance with the invention (e.g., A0-736, BHT and E-376) provide % polymer inhibition protection results that are greater than the sum of the individual component protection results at comparable treatment dosages when the range of phenylenediamine:hindered phenol is in the range of 2:1 to 1:2 (by weight). In those test runs in which a 1:3 ratio of phenylenediamine:hindered phenol is employed, the % protection results are less than that provided by the sum of the individual component protection results at comparable treatment dosages.

The test results further reveal that combinations of phenylenediamine (RROA) with a hindered phenol that is not substituted at the para position (with respect to the hydroxyl group), namely DTBP, do not provide unexpected results since the calculated percent protection found by "additivity" of the individual component treatments is greater than the actually "found" results for the combinations. Accordingly, a hindered phenol, in accordance with the invention, must have a substituent, as above defined, at the 4-position on the phenol ring.

Based upon these results, at present, it is preferred to utilize a 1:1 combination of phenylenediamine (RROA) with BHT.

Due to the unexpected results shown by the combinations of phenylenediamine and hindered phenol, it is possible to produce a more effective styrene monomer anti-polymerization treatment than is obtainable by the use of either individual ingredient alone when measured at comparable treatment levels. Because of the enhanced polymerization inhibiting activity of the mixture, the concentration of each of the ingredients may be lowered and the total quantity of the polymerization inhibitor required for an effective treatment at elevated temperatures may be reduced. This factor is especially important in monomer purification procedures where the obvious goal of the process is to provide high level monomer purity.

The term "elevated temperatures" as used herein means temperatures of from about 100°–300° F. that are commonly utilized during the heat treatment of styrene monomers. Such heat treatment processes include distillation and sundry other procedures.

The methods and compositions of the present invention can control the fouling of processing equipment, such as equipment used in the separation and purification processes of styrene monomers, which is due to or caused by the polymerization of the styrene monomers. The instant invention is useful as a process inhibitor, which is employed during the preparation and processing of the monomer. The invention can be utilized under normal pressure (760 mm), under superatmospheric pressure or under reduced pressure. The phenylenediamine or derivatives thereof and the hindered phenol can be provided to the monomer by any conventional method. The components can be added to the monomer as a single composition containing the inhibitor compounds or the individual components can be added separately or in any other desired combination.

While this invention has been described with respect to particular embodiments thereof, it is apparent that numerous other forms and modifications will be obvious to those skilled in the art. The appended claims generally should be construed to cover all such obvious forms and modifications which are within the true spirit and scope of the present invention.

What is claimed is:

1. A method of inhibiting polymerization of a vinyl aromatic compound monomer comprising adding to the vinyl aromatic compound monomer an effective inhibiting amount of (a) a phenylenediamine compound having at least one N—H bond therein, and (b) a hindered phenol having the structure

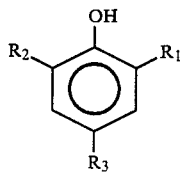

wherein $R_1$ and $R_2$ may be the same or different, with $R_1$ and $R_2$ being independently chosen and selected from the group of $C_1$–$C_{20}$ alkyl, $C_1$–$C_{30}$ alkaryl, and substituted $C_1$–$C_{30}$ alkaryl; $R_3$ is selected from the group of $C_1$–$C_{20}$ alkyl, thiophenol, substituted thiophenol, $C_1$–$C_{40}$ alkanoic acid ester, $C_1$–$C_{30}$ alkaryl, substituted $C_1$–$C_{30}$ alkaryl, $C_1$–$C_6$ alkylamino, $C_1$–$C_6$ alkoxy, amine, polynuclear aryl and substituted polynuclear aryl.

2. A method as recited in claim 1 wherein said vinyl aromatic compound comprises styrene.

3. A method as recited in claim 2 wherein said phenylenediamine compound (a) has the structure

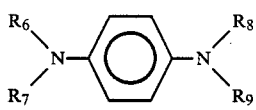

wherein $R_6$, $R_7$, $R_8$, and $R_9$ are the same or different and are hydrogen, alkyl, alkaryl, or aralkyl, with the proviso that at least one of $R_6$, $R_7$, $R_8$ or $R_9$ is hydrogen.

4. A method as recited in claim 3 wherein $R_6$, $R_7$, $R_8$, and $R_9$ each have from 1–20 carbon atoms except for at least one of $R_6$, $R_7$, $R_8$ or $R_9$ that is hydrogen.

5. A method as recited in claim 4 wherein (a) comprises N-phenyl-N'-(1,4-dimethyl-pentyl)-p-phenylenediamine.

6. A method as recited in claim 1 wherein $R_1$ and $R_2$ are each independently chosen from $C_1$–$C_{20}$ tert-alkyl and $C_1$–$C_{20}$ alkyl.

7. A method as recited in claim 6 wherein $R_3$ is chosen from $C_1$–$C_{20}$ alkyl, $C_1$–$C_{40}$ alkanoic acid ester, thiophenol and substituted thiophenol having the structure

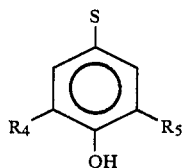

wherein $R_4$ and $R_5$ are each independently selected from $C_1$–$C_6$ alkyl.

8. A method as recited in claim 7 wherein $R_1$ and $R_2$ are both tert-butyl and wherein $R_3$ is methyl.

9. A method as recited in claim 1 wherein the weight ratio of (a):(b) is from about 2:1 to about 1:2.

10. A method as recited in claim 9 wherein the amount of (a) and (b) added, collectively, to said monomer is from about 1–10,000 ppm per one million parts of said monomer.

11. A method as recited in claim 10 wherein the amount of (a) and (b) added, collectively, to said monomer is from about 1–1000 ppm.

12. A method as recited in claim 1 further comprising heating said monomer.

13. A method as recited in claim 1 further comprising distilling said monomer to remove impurities therefrom.

14. Vinyl aromatic monomer anti-polymerization composition comprising a liquid carrier and dissolved or dispersed therein (a) a phenylenediamine compound having at least one N—H bond therein, and (b) a hindered phenol having the structure

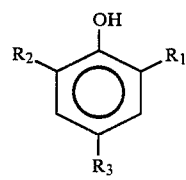

wherein $R_1$ and $R_2$ may be the same or different, with $R_1$ and $R_2$ being independently chosen and selected from the group of $C_1$–$C_{20}$ alkyl, $C_1$–$C_{30}$ alkaryl, and substituted $C_1$–$C_{30}$ alkaryl; $R_3$ is selected from the group of $C_1$–$C_{20}$ alkyl, thiophenol, substituted thiophenol, $C_1$–$C_{40}$ alkanoic acid ester, $C_1$–$C_{30}$ alkaryl, substituted $C_1$–$C_{30}$ alkaryl, $C_1$–$C_6$ alkoxy, polynuclear aryl and substituted polynuclear aryl.

15. Vinyl aromatic monomer anti-polymerization composition as recited in claim 14 wherein (a) and (b) are present in a weight ratio (a):(b) of from about 2:1 to 1:2.

16. Vinyl aromatic monomer anti-polymerization composition as recited in claim 14 wherein (a) has the structure

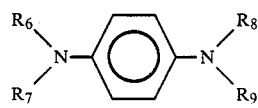

wherein $R_6$, $R_7$, $R_8$, $R_9$ are the same or different and are hydrogen, alkyl, aryl, alkaryl or aralkyl with the proviso that at least one of $R_6$, $R_7$, $R_8$ or $R_9$ is hydrogen.

17. Vinyl aromatic monomer anti-polymerization composition as recited in claim 16 wherein $R_6$, $R_7$, $R_8$, and $R_9$ each have from 1–20 carbon atoms except for at least one of $R_6$, $R_7$, $R_8$, or $R_9$ that is hydrogen.

18. Vinyl aromatic monomer anti-polymerization composition as recited in claim 17 wherein (a) comprises N-phenyl-N'-(1,4-dimethylpentyl)-p-phenylenediamine.

19. Vinyl aromatic monomer anti-polymerization composition as recited in claim 14 wherein $R_1$ and $R_2$ are each independently chosen from $C_1$–$C_{20}$ tert-alkyl and $C_1$–$C_{20}$ alkyl.

20. Vinyl aromatic monomer anti-polymerization composition as recited in claim 19 wherein $R_3$ is chosen from $C_1$–$C_{20}$ alkyl, $C_1$–$C_{40}$ alkanoic acid ester, thiophenol and substituted thiophenol having the structure

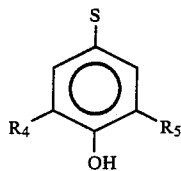

wherein R4 and R5 are each independently selected from $C_1$–$C_6$ alkyl.

21. Vinyl aromatic monomer anti-polymerization composition as recited in claim 20 wherein $R_1$ and $R_2$ are both tert-butyl and wherein $R_3$ is methyl.

22. Vinyl Aromatic monomer anti-polymerization composition as recited in claim 14 wherein said liquid carrier comprises a non-polar organic solvent and wherein (a) and (b) are both dissolved in said solvent.

23. Vinyl aromatic monomer anti-polymerization composition as recited in claim 22 wherein said non-polar organic solvent comprises heavy aromatic naphtha or xylene.

24. Vinyl aromatic monomer anti-polymerization composition as recited in claim 14 further comprising styrene monomer.

25. A method of inhibiting polymerization of a vinyl aromatic compound monomer comprising adding to the vinyl aromatic compound monomer an effective inhibiting amount of (a) phenylenediamine compound having at least one N—H bond therein, and (b) a hindered phenol, said hindered phenol having the structure

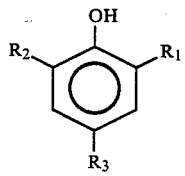

wherein $R_1$ is methyl, $R_2$ is tert-butyl and $R_3$ is substituted thiophenol having the structure

wherein R4 is methyl and R5 is tert-butyl.

26. A method of inhibiting polymerization of a vinyl aromatic compound monomer comprising adding to the vinyl aromatic compound monomer an effective inhibiting amount of (a) a phenylenediamine compound having at least one N—H bond therein, and (b) a hindered phenol, said hindered phenol having the structure

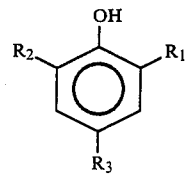

wherein $R_1$ and $R_2$ are both tert-butyl and wherein $R_3$ is an alkanoic acid ester.

27. A method as recited in claim 26 wherein R3 comprises octadecyl propionate.

28. Vinyl aromatic monomer anti-polymerization composition comprising a liquid carrier and dissolved or dispersed therein (a) a phenylenediamine compound having at least one N—H bond therein, and (b) a hindered phenol having the structure

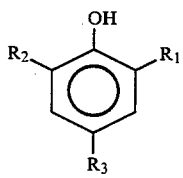

wherein $R_1$ is methyl, $R_2$ is tert-butyl and $R_3$ is substituted thiophenol having the structure

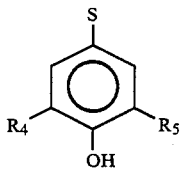

wherein R4 is methyl and R5 is tert-butyl.

29. Vinyl aromatic anti-polymerization composition comprising a liquid carrier and dissolved or dispersed therein (a) a phenylenediamine compound having at least one N—H bond therein, and (b) a hindered phenol having the structure

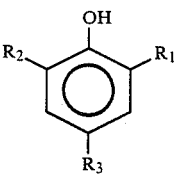

wherein $R_1$ and $R_2$ are both tert-butyl and wherein $R_3$ is an alkanoic acid ester.

30. A composition as recited in claim 29 wherein R3 comprises octadecyl propionate.

* * * * *